United States Patent
Krieg et al.

(10) Patent No.: US 12,401,953 B2
(45) Date of Patent: Aug. 26, 2025

(54) METHOD FOR OPERATING A HEARING AID AND HEARING AID

(71) Applicant: Sivantos Pte. Ltd., Singapore (SG)

(72) Inventors: Julius Krieg, Erlangen (DE); Christoph Kukla, Erlangen (DE)

(73) Assignee: Sivantos Pte. Ltd., Singapore (SG)

( * ) Notice: Subject to any disclaimer, the term of this patent is extended or adjusted under 35 U.S.C. 154(b) by 302 days.

(21) Appl. No.: 18/184,070

(22) Filed: Mar. 15, 2023

(65) Prior Publication Data

US 2023/0300541 A1 Sep. 21, 2023

(30) Foreign Application Priority Data

Mar. 15, 2022 (DE) ...................... 10 2022 202 568.7

(51) Int. Cl.
H04R 25/00 (2006.01)
(52) U.S. Cl.
CPC ............. H04R 25/30 (2013.01); H04R 25/65 (2013.01)
(58) Field of Classification Search
CPC ..... A61B 5/01; A61B 5/02438; A61B 5/1116; A61B 2562/0219; H04R 25/30; H04R 25/65; H04R 25/507; H04R 2225/00
See application file for complete search history.

(56) References Cited

U.S. PATENT DOCUMENTS

2014/0235968 A1 8/2014 LeBoef et al.

FOREIGN PATENT DOCUMENTS

| DE | 102015219573 A1 | 4/2017 |
| EP | 3154278 A1 | 4/2017 |
| WO | 2016176668 A1 | 11/2016 |
| WO | 2021188360 A1 | 9/2021 |

OTHER PUBLICATIONS

English Translation of EP 3154278 (Year: 2017).*
Cleveland Clinic: "Positions to Reduce Shortness of Breath", http://www.archive.org Dec. 21, 2018 URL: https://web.archive.org/web/20200808032321/https://my.clevelandclinic.org/health/articles/9446-positions-to-reduce-shortness-of-breath [retrieved Mar. 17, 2023].

* cited by examiner

*Primary Examiner* — Brian Ensey
(74) *Attorney, Agent, or Firm* — Laurence A. Greenberg; Werner H. Stemer; Ralph E. Locher

(57) ABSTRACT

A method operates a hearing aid, which has a sensor, a microphone, and a receiver. Breathing difficulties of a wearer are inferred on the basis of measurement data created by the sensor and a measure for a risk is determined based thereon. An activity helping the wearer is carried out depending on the measure. Furthermore, the hearing aid is configured for carrying out the method.

9 Claims, 5 Drawing Sheets

METHOD FOR OPERATING A HEARING AID AND HEARING AID

CROSS-REFERENCE TO RELATED APPLICATION

This application claims the priority, under 35 U.S.C. § 119, of German Patent Application DE 10 2022 202 568.7, filed Mar. 15, 2022; the prior application is herewith incorporated by reference in its entirety.

FIELD AND BACKGROUND OF THE INVENTION

The invention relates to a method for operating a hearing aid and a hearing aid. The hearing aid has a sensor, a microphone, and a receiver in each case. The hearing aid is preferably a hearing aid device.

Persons who suffer from a loss of the sense of hearing typically use a hearing aid device. In this case, an ambient sound is usually converted into an electrical (audio/sound) signal by means of a microphone, thus an electromechanical sound transducer, so that the electrical signal is acquired. The acquired electrical signals are processed by means of an amplifier circuit and introduced by means of a further electromechanical transducer in the form of a receiver into the auditory canal of the person. Moreover, the acquired sound signals are usually processed, for which purpose a signal processor of the amplifier circuit is typically used. The amplification is adapted in this case to a possible loss of hearing of the hearing aid wearer.

Breathing difficulties ("dyspnea") occur in up to one-fourth of the world population. Breathing is more difficult for the respective person in this case, so that a level of comfort is reduced. Due to the labored breathing, fear and panic states can be induced in this case. However, in addition to the subjectively unpleasant experience, still further effects can additionally occur, which can sometimes be life-threatening. Such labored breathing (breathing difficulties) can occur acutely, in particular in certain situations, such as after a physical exertion. However, it can also be chronic. Breathing difficulties can occur as a symptom of asthma, stress, allergic reactions, a cardiac disease, or other diseases. Therefore, medical care of the respective person is necessary depending on the respective reason for presently occurring breathing difficulties, or certain activities are to be carried out by the person.

SUMMARY OF THE INVENTION

The invention is based on the object of specifying a particularly suitable method for operating a hearing aid and a particularly suitable hearing aid, wherein in particular a functional scope and/or a level of safety is increased for a wearer.

This object is achieved according to the invention with respect to the method by the features of the independent method claim and with respect to the hearing aid by the features of the independent hearing aid claim. Advantageous refinements and embodiments are the subject matter of the respective dependent claims.

The method is used for operating a hearing aid. For example, the hearing aid is a headphone or comprises a headphone. Alternatively, the hearing aid is a headset, true wireless headphone, hearable, or personal sound amplifier. However, the hearing aid is particularly preferably a hearing aid device. The hearing aid device is used to assist a person suffering from a loss of the sense of hearing. In other words, the hearing aid device is a medical device by means of which, for example, a partial hearing loss is compensated for. The hearing aid device is, for example, a "receiver-in-the-canal" hearing aid device (RIC; ex-receiver hearing aid device), an in-ear hearing aid device, such as an "in-the-ear" hearing aid device, an "in-the-canal" hearing aid device (ITC), or a "complete-in-canal" hearing aid device (CIC), hearing aid glasses, a pocket hearing aid device, a bone vibrator hearing aid device, or an implant. In a further alternative, the hearing aid device is a behind-the-ear hearing aid device, which is worn behind a pinna.

The hearing aid is provided and configured to be worn on the human body. In other words, the hearing aid preferably contains a holding device, by means of which fastening on the human body is possible. If the hearing aid is a hearing aid device, the hearing aid is provided and configured, for example, to be arranged behind the ear or inside an auditory canal. In particular, the hearing aid is wireless and is provided and configured to be inserted at least partially into an auditory canal. The hearing aid particularly preferably comprises an energy storage device, by means of which an energy supply is provided.

The hearing aid furthermore comprises a microphone, which is used to acquire sound. In particular, an ambient sound, or at least a part thereof, is acquired by means of the microphone during operation. The microphone is in particular an electromechanical sound transducer. The microphone has, for example, only one single microphone unit or multiple microphone units, which interact with one another. Each of the microphone units expediently has a membrane, which is set into vibrations by means of soundwaves, wherein the vibrations are converted by means of a corresponding pickup device, such as a magnet moved in a coil, into an electrical signal. It is thus possible to acquire an audio signal by means of the respective microphone unit which is based on the sound incident on the microphone unit. The microphone units are designed in particular as unidirectional. The microphone is expediently arranged at least partially inside a housing of the hearing aid and is thus at least partially protected.

Furthermore, the hearing aid has a receiver to output an output signal. The output signal is in particular an electrical signal in this case. The receiver is an electromechanical sound transducer, preferably a loudspeaker. Depending on the design of the hearing aid, in the intended state the receiver is arranged at least partially inside an auditory canal of a wearer of the hearing aid, thus a person, or is at least acoustically connected thereto. The hearing aid is primarily used in particular to output the output signal by means of the receiver, wherein speaking sound is created. In other words, the main function of the hearing aid is the output of the output signal. The output signal is at least partially created in particular depending on the sound acquired by means of the microphone. Alternatively, the output signal is created depending on a transmitted data signal, or the data signal is used for this purpose. In other words, the output signal is created in particular by means of a streaming process, or this involves a reproduction of a specific sample.

The hearing aid furthermore has a sensor, by means of which measurement data are created during operation. The sensor is formed in this case, for example, by means of a single unit or comprises different units. It is thus possible, for example, to acquire different signals by means of the sensor, which are based in particular on different physical conditions, or which result at different locations, wherein a corresponding unit of the sensor is arranged at each of these locations. For example, the sensor is formed by means of the microphone or comprises it. Alternatively thereto, the sensor and the microphone are components of the hearing aid separate from one another. The measurement data suitably correspond to the signal which is acquired by means of the sensor. The measurement data are in particular electrical signals. Exemplary embodiments of sensors which acquire, generate, or form these measurement data are: an electroencephalography sensor, an electrocardiography sensor, a photoplethysmography sensor, a near infrared spectroscopy sensor, an electrooculography sensor, an electromyography sensor, a sensor for muscle tension, a pupillometry sensor, a micro-expression sensor, a sensor for acquiring respiratory parameterization, a respiratory depth sensor, a respiratory frequency sensor, a heart rate sensor, a sensor for heart rate variability, a blood pressure sensor, a sensor for a contractile property of the heart, a microphone, an inertial measurement unit, a vibrometer, a cortisol sensor, a sweat sensor, a sensor for the skin conduction value, a temperature sensor, a sensor for the oxygen saturation of the blood, a bioimpedance sensor, an auscultatory sensor, a capnometry sensor.

According to the method, breathing difficulties of the wearer of the hearing aid are inferred on the basis of measurement data created by means of the sensor. The measurement data are in particular such that breathing difficulties of the wearer can be inferred on the basis thereof, and the sensor is designed accordingly. In summary, initially the measurement data are created and these are analyzed and/or evaluated. It is derived on the basis of the measurement data whether the wearer suffers from breathing difficulties presently or at least at the point in time of the signal corresponding to the measurement data. A measure of a risk is determined based thereon. In other words, a measure of a risk for the wearer is derived in particular on the basis of the presence of the breathing difficulties. For example, the measure is solely binary and one state is used if the breathing difficulties exist and otherwise the other state. Alternatively thereto, for example, the measure has multiple steps, wherein only the presence of the breathing difficulties is used for the assignment of the respective value of the measure or, particularly preferably, still further parameters are. For example, a severity of the breathing difficulties is also used for the determination of the measure of the risk. In particular, a threshold value comparison is carried out for this purpose.

An activity which helps the wearer is carried out depending on the measure. The helping activity is in this case such that the wearer is assisted in their present situation, thus upon the presence of the breathing difficulties, so that they are relieved. The activity relates in this case to the breathing difficulties, and this ensures, for example, that the breathing difficulties are decreased, and/or that the wearer of the hearing aid is assisted in managing the situation, in which the breathing difficulties occur.

For example, the activity is only carried out if the measure of the risk exceeds a certain threshold value. Alternatively, for example, different activities are present for selection, wherein the respective activity is carried out depending on the measure. In other words, different activities are carried out in the case of different measures for the risk.

An activity helping the wearer of the hearing aid is thus carried out on the basis of the method when this wearer suffers from breathing difficulties, which in particular represent a comparatively high risk. The risk is therefore preferably reduced for the wearer of the hearing aid. A level of comfort is at least increased for the wearer of the hearing aid, who is also referred to as the user. A functional scope of the hearing aid is also enlarged in this way. Respiratory distress can be, for example, a symptom of a chronic obstructive lung disease (worldwide prevalence approximately 7-19%), bronchial asthma (worldwide prevalence approximately 5%), physical strain such as sports or exhausting coughing, psychological stress, allergic reactions, diseases of the heart, a cardiac insufficiency, an acute coronary syndrome with retrosternal discomfort and breathing difficulties, COVID-19, and further pathological states affecting the lungs, such as a pneumonia, a pneumothorax, or a lung embolism. Acute breathing difficulties can result in suffocation. Accompanying systems of a disease inducing breathing difficulties can also damage health if a treatment does not occur or takes place too late. Breathing difficulties are to be registered since they can have a more severe manifestation in other situations, for example in the event of increased physical strain or changed environmental conditions.

As soon the breathing difficulties have been inferred, this is preferably stored in a memory so that a log of this is present. The memory is, for example, a component of the hearing aid or an external device having a communication connection thereto. In particular, the respective point in time is additionally also stored. This takes place in particular independently of the measure of the risk, so that a corresponding entry in the log always takes place when breathing difficulties are present. The measure of the risk and/or the possible activity which is carried out is preferably additionally also stored. In one refinement, for example, a possible acoustic classification and/or other operating data are also stored. Alternatively thereto, the storage only takes place when the measure of the risk exceeds or corresponds to a certain value. In this way, a space required for the log is reduced. A determination of a health condition of the wearer is made possible in a separate diagnostic method on the basis of the log.

A current posture of the wearer is particularly preferably determined on the basis of the measurement data. The breathing difficulties are then inferred therefrom. In particular, the breathing difficulties are inferred when a certain posture has been assumed by the wearer. The breathing difficulties are suitably inferred when a pre-tension of muscles, which are required for breathing or at least assist it, takes place in the posture. In particular a pressure in the abdominal area and/or in the rib area of the wearer takes place due to the specific posture. The breathing difficulties are preferably inferred here if the respective posture is maintained for at least a certain time span. The time span is preferably 5 seconds, 10 seconds, or 30 seconds here.

Some postures have the effect of facilitating breathing in that they pre-tension the auxiliary respiratory muscles in a favorable amount. Auxiliary respiratory muscles assist, for example, the elevation or depression of ribs or the abdominal pressure. Some auxiliary respiratory muscles assist inhaling, some assist exhaling. Different muscles are tensioned or pre-tensioned by a different amount depending on the posture. Throat, neck, shoulder, torso, chest, abdominal, or back musculature which can assist the breathing can be selected from the following group of muscles: musculus sternocleidomastoideus, musculi scaleni, musculus scalenus anterior, musculus scalenus medius, musculus scalenus posterior, musculus latissimus dorsi, musculus transversus thoracis, musculi pectorales, musculus pectoralis major, musculus pectoralis minor, musculi serrati, musculus serratus posterior superior, musculus serratus posterior inferior, musculus serratus anterior, musculus rectus abdominis, musculus transversus abdominis, musculus obliquus externus abdominis, musculus obliquus internus abdominis, musculus quadratus lumborum.

The so-called cart driver position is used as the defined posture or one of the defined postures, for example. In this position, the wearer is seated, wherein the upper body is inclined forward and the head is directed downward. The arms are also supported on the thighs. The sensor is preferably an acceleration sensor and/or position sensor or comprises at least these sensors in this case. In particular, the measurement data, on the basis of which the cart driver position is inferred, correspond to a circular forward movement of the head which is ended abruptly, and/or to a rotation around a transverse axis, for example at the height of the pelvis of the wearer.

Another such (defined) posture is the so-called pasha position, in which the wearer sits with a fully straightened back and slightly inclined head. The duration which this posture is maintained is greater than a stretching movement is long and is in particular longer than 10 seconds. The sensor also is or comprises, for example, an acceleration and/or position sensor here, and the measurement data correspond to stretching of the spinal column.

Another such (defined) posture is standing bent over, wherein the arms are supported, for example on a chair or on a wall. In particular, in this case the measurement data correspond to a movement of the head in a circular arc, which is ended abruptly. Another such (defined) posture is standing leaning to the rear, wherein the back is supported, for example on a wall, and wherein the head is inclined slightly downward. In particular, in this case the measurement data also correspond to a movement of the head in a circular arc.

The two above-mentioned defined postures, in which the head of the wearer is located in the area of a wall and thus the microphone is also located at a comparatively small distance from the wall, are also determinable on the basis of the electrical signals created by means of the microphone, since the sound thus acquired has specific properties. In particular, in this case the determined posture is additionally confirmed by means of the microphone, or the signals created by means of the microphone are at least partially used as measurement data, so that the microphone at least partially forms the sensor.

Another such (defined) posture is, for example, the crouch, wherein the hands are supported on the knees or the thighs. The head is directed in the direction of the ground in this case.

One of the above-mentioned (defined) postures is assumed by the wearer, sometimes unconsciously, for example, in order to facilitate the breathing, wherein this is independent of the age and sex of the wearer. The breathing difficulties therefore exist when the wearer assumes one of the defined postures, which is determined by means of the sensor. Due to the determination of the breathing difficulties on the basis of the posture, it is not necessary to directly acquire vital functions of the wearer, because of which a hardware requirement is reduced. This is also independent of the age and sex of the wearer, because of which it is not necessary to perform a special setting of the hearing aid. The hearing aid is thus usable by different persons as wearers.

For example, the determined posture is also used in determining the measure of the risk. Thus, for example, some of the defined postures are used in the case of a higher risk and others in the case of a lower risk.

Alternatively or in combination therewith, a value characterizing the respiration of the wearer is determined on the basis of further measurement data created by means of the microphone. For example, the respiratory frequency or a depth of the respiration, which corresponds to an inhaled air volume, is used as a characterizing value, or the characterizing value comprises at least one thereof. Alternatively or in combination therewith, for example, the characterizing value comprises the presence and/or a strength of a murmur or rattling during breathing, for example during inhalation or preferably during exhalation. Such a murmur occurs in particular if the lips of the wearer are pressed together so that a counter pressure results during exhalation, which facilitates respiration. This takes place in particular because the bronchi are expanded.

The characterizing value is used to infer the breathing difficulties. Since the microphone is already present, no additional components are therefore required, because of which production costs of the hearing aid are reduced. For example, the microphone represents the sensor here, and the further measurement data correspond to the measurement data, so that production costs are reduced further. However, the sensor and the microphone are particularly preferably provided which represent separate components from one another in particular. The accuracy when concluding the breathing difficulties is thus improved.

For example, the breathing difficulties are inferred on the basis of an algorithm based on the measurement data. The algorithm is, for example, permanently stored or adapted to the respective wearer. However, a neural network is particularly preferably used to infer the breathing difficulties. This is trained in particular during the wearing of the hearing aid by the wearer, wherein the neural network has, for example, at least rudimentary training even before the first use. Therefore, an accuracy in determining the breathing difficulties is increased with increasing wearing duration and the hearing aid is thus adapted to the respective wearer. In this way, no accurate knowledge about the physique of the wearer is also required in the production of the hearing aid.

Alternatively or in combination therewith, the neural network is used to predict breathing difficulties, so that the measure of the risk in particular represents a measure of the occurrence of the breathing difficulties. An actual occurrence of the breathing difficulties is prevented or its strength is at least reduced in this case by means of carrying out the helping activity. A level of comfort for the wearer of the hearing aid is thus further increased.

For example, the determination of the measure of the risk takes place independently of further parameters and, for example, solely on the basis of the measurement data. However, further influencing factors/parameters are particularly preferably taken into consideration. A determined physical activity of the wearer is preferably taken into consideration in the determination of the measure of the risk. In other words, it is determined that the wearer carries out a physical activity or does not before the occurrence or upon the occurrence of the breathing difficulties. For example, the same measurement data or different measurement data are used to determine the physical activity which were created earlier with respect to time by means of the or another sensor. In this way, it can be derived, for example, whether the breathing difficulties occur due to the physical activity, for example a sports activity, and/or a comparatively strong physical strain, such as climbing stairs. Since in this case the breathing difficulties diminish after a comparatively short time span, the measure of the risk is reduced. In other words, a reduced measure of the risk is used if a physical activity was carried out by the wearer before occurrence of the breathing difficulties. In contrast, if the breathing difficulties occur when essentially no physical activity took place earlier with respect to time, the measure of the risk is increased.

Particularly preferably, external data which relate to the physical condition of the wearer are received from an external sensor according to the method. The external sensor is, for example, mobile, wearable, fastenable on the clothing, implantable, and/or a terminal. In particular, the external data are created by means of the external sensor and are also, for example, measurement data, or the external data are already at least partially evaluated measurement data. An electrocardiography sensor (ECG), an auscultation sensor, a photoplethysmography sensor, or a ballistocardiography sensor is used as such an external sensor, for example. Alternatively or in combination therewith, the external data relate or correspond to a pulse frequency, a change of the pulse, a blood pressure, an oxygen content of the blood, a body temperature, a skin temperature, a respiratory frequency, or a respiratory depth. In a further alternative, the external data relate to a perspiration of the wearer, which are created in particular on the basis of an electrodermal activity, for example of a sensor for the skin conduction value, and/or by means of a VCSEL laser and a photodetector. The external data are used in determining the measure of the risk. Thus, for example, a higher measure of the risk is used in the event of an elevated blood pressure and/or elevated perspiration than in the event of a lower blood pressure/little perspiration. Alternatively or in combination therewith, external data are also used to infer the breathing difficulties. Exemplary embodiments of such an external sensor are, for example: an electroencephalography sensor, an electrocardiography sensor, a photoplethysmography sensor, a near infrared spectroscopy sensor, an electrooculography sensor, an electromyography sensor, a sensor for muscle tension, a pupillometry sensor, a micro-expression sensor, a sensor for acquiring respiratory parameterization, a respiratory depth sensor, a respiratory frequency sensor, a heart rate sensor, a sensor for heart rate variability, a blood pressure sensor, a sensor for a contractile property of the heart, a microphone, an inertial measurement unit, a vibrometer, a cortisol sensor, a sweat sensor, a sensor for the skin conduction value, a temperature sensor, a sensor for the oxygen saturation of the blood, a bioimpedance sensor, an auscultatory sensor, a capnometry sensor.

The external sensor is preferably a component of an external device which is worn by the wearer and is coupled for signaling to the hearing aid, for example. In particular, the hearing aid has a corresponding device for this purpose. The coupling with respect to signals expediently takes place by means of radio, thus wirelessly. Alternatively thereto, they are coupled for signaling in a wired manner. The external device is in particular a fitness armband or a mobile telephone, such as a smartphone. The invention also relates to a system having the hearing aid and the external device which has the external sensor.

In one refinement of the method, a current environmental situation is determined, wherein this takes place in particular after the breathing difficulties have been inferred. Alternatively or in combination therewith, the environmental situation is already used for the operation of the hearing aid, in particular for the operation of the receiver. The helping activity is preferably carried out in dependence on the current environmental situation. Thus, in particular in the case of a moderate measure of the risk and an environmental situation in which further persons are present, a request, in particular a request in the form of a message, is output thereto to help the wearer of the hearing aid. For this purpose, in particular a speaking sound signal is output, for example by means of the receiver or a further output device. Alternatively, for example, an alarm is triggered on a smartphone or another device. In a further alternative, for example, a further hearing aid wearer is alarmed, wherein the request is output by means of their receiver. The request is exchanged here between the two hearing aids, preferably via a peer2peer network.

If the current environmental situation corresponds, for example, to a theater or opera visit, the output only takes place, in contrast, in the case of a comparatively large measure of the risk. In contrast, when participating in road traffic, the output is already carried out in the case of a reduced measure so that further road users are notified of the restricted health condition of the wearer, even if, for example, it is not necessary to help them. The output takes place here, for example, on mobile devices of persons in the vicinity and/or on a terminal device, for example a large display panel, which is visible to a group of persons in the vicinity and announces the emergency situation and parameters characterizing it (e.g., type of the problem, location, direction or distance of the wearer).

Alternatively or in combination therewith, the measure of the risk is also determined on the basis of the current environmental situation. Thus, for example, upon assuming a posture, on the basis of which the breathing difficulties are inferred or can be inferred, and which has a comparatively unnatural appearance, a comparatively high risk is assumed if it is inferred on the basis of the current environmental situation that the wearer is located in public. If this posture is assumed in spite of being in public, it is presumed that the breathing difficulties are comparatively strong. In contrast, if this posture is assumed in private spaces, thus is used in particular when no further person is present, a reduced measure is used for the risk.

For example, the helping activity comprises the output of an instruction to assume a posture more strongly assisting the respiration. The instruction is preferably output in this case by means of the receiver, so that the instruction is perceptible at least to the wearer of the hearing aid. In particular, the output of the instruction takes place in such a way that it is essentially only perceptible by the wearer of the hearing aid. When the wearer of the hearing aid assumes the posture more strongly assisting the respiration, certain muscles of the wearer are pre-tensioned so that the respiration is facilitated for the wearer. In particular, one of the above-mentioned defined postures is used for this purpose. If the presence of the breathing difficulties has already been inferred on the basis of the posture, in particular another of the defined postures is specified in the instruction in which the respiration is assisted more strongly, thus which relieves the breathing difficulties more strongly than in the present posture of the wearer.

Alternatively or in combination therewith, the helping activity comprises sending an emergency message by means of a communication device of the hearing aid. This helping activity is preferably only carried out in the case of a comparatively high measure of the risk. The emergency message is in particular directed to a rescue coordinating center, an emergency service, and/or an emergency physician. In this way, a reaction time to the medical care of the wearer by these services is reduced. The communication device is in particular operated according to a mobile wireless and/or WLAN standard, and the emergency message is sent directly from the hearing aid to the desired receiver of the emergency message. Alternatively thereto, the communication device is operated according to a Bluetooth standard and is directed, for example, to the possible external device, which is a mobile telephone, for example. The emergency message is then correspondingly transmitted further therefrom in accordance with a mobile wireless and/or WLAN standard. In this way, an energy consumption for the operation of the hearing aid is reduced, wherein the emergency message is nonetheless reliably transmitted.

The hearing aid has a microphone and a receiver, between which in particular a signal processing unit is connected for signaling. In particular a signal path is formed by means of this, and the microphone is preferably used to acquire sound and the receiver is suitably used to output sound. For example, the hearing aid is a headphone or comprises a headphone. In this case, the hearing aid is configured, for example, as a so-called headset. However, the hearing aid is particularly preferably a hearing aid device. The hearing aid device is used to assist persons suffering from a loss of the sense of hearing. In other words, the hearing aid device is a medical device by means of which, for example, a partial hearing loss is compensated for. The hearing aid device is, for example, a "receiver-in-the-canal" hearing aid device (RIC; ex-receiver hearing aid device), an in-ear hearing aid device, such as an "in-the-ear" hearing aid device, an "in-the-canal" hearing aid device (ITC), a "complete-in-canal" hearing aid device (CIC) or an "invisible in the canal" hearing aid device (IIC), hearing aid glasses, or a pocket hearing aid device. Particularly preferably, the hearing aid device is a behind-the-ear hearing aid device, which is worn behind a pinna. Furthermore, the hearing aid has a sensor for creating measurement data. In particular, it is made possible to infer breathing difficulties of the wearer on the basis of the measurement data in this case. The sensor is suitably constructed and/or designed for this purpose.

The hearing aid is operated according to a method in which, on the basis of measurement data created by means of the sensor, breathing difficulties of a wearer are inferred and a measure of a risk is determined based thereon. An activity helping the wearer is carried out depending on the measure, so that the wearer is helped in particular directly or as a consequence of followed instructions. For example, the breathing difficulties are inferred, the measure of the risk is determined, and/or the activity is carried out by means of the signal processing unit. In other words, the signal processing unit is suitable, in particular provided and configured, to at least partially carry out the method.

The hearing aid expediently contains a signal processor, which suitably forms the signal processing unit or is at least one component thereof. The signal processor is, for example, a digital signal processor (DSP) or is implemented by means of analog components. An adaptation of the signal created by means of the microphone is in particular also carried out by means of the signal processor, preferably depending on a possible hearing loss of a wearer of the hearing aid. An A/D converter is expediently arranged between the microphone and the signal processing unit, for example the signal processor, if the signal processor is configured as a digital signal processor. The signal processor is set in particular depending on a parameter set. An amplification in different frequency ranges is predetermined here by means of the parameter set, so that the signal created by means of the microphone is processed according to defined specifications, in particular depending on a hearing loss of the wearer of the hearing aid. The hearing aid particularly preferably additionally comprises an amplifier, or the amplifier is at least partially formed by means of the signal processor. For example, the amplifier is connected upstream or downstream of the signal processor for signaling.

The refinements and advantages described in conjunction with the method are also to be transferred accordingly to the hearing aid and vice versa.

Other features which are considered as characteristic for the invention are set forth in the appended claims.

Although the invention is illustrated and described herein as embodied in a method for operating a hearing aid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Parts corresponding to one another are provided with the same reference signs in all figures.

Figure 1:
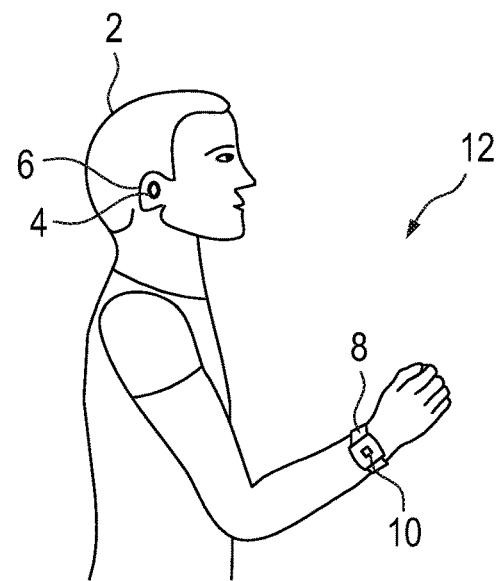
FIG. 1 is an illustration showing a wearer of a hearing aid.

Referring now to the figures of the drawings in detail and first, particularly to FIG. 1 thereof, there is shown a wearer 2 of a hearing aid 4 in the form of a hearing aid device, which is provided and configured to be worn behind an ear 6 of the wearer 2 (user, hearing aid wearer). In other words, it is a "behind-the-ear" hearing aid device. The wearer 2 furthermore has an external device 8 in the form of a fitness armband, which has an external sensor 10. It is possible by means of the external sensor 10 to measure a pulse rate of the wearer 2. The external device 8 moreover comprises a communication module, which is operated according to a mobile wireless standard. It is thus possible for the wearer 2 to make telephone calls and/or receive data by means of the external device 8. The communication module is also additionally capable of establishing a Bluetooth connection. In intended use, the external device 8 and the hearing aid 4 are connected for signaling by means of a Bluetooth connection, so that a system 12 is formed, which comprises the external device 8 and the hearing aid 4.

Figure 2:
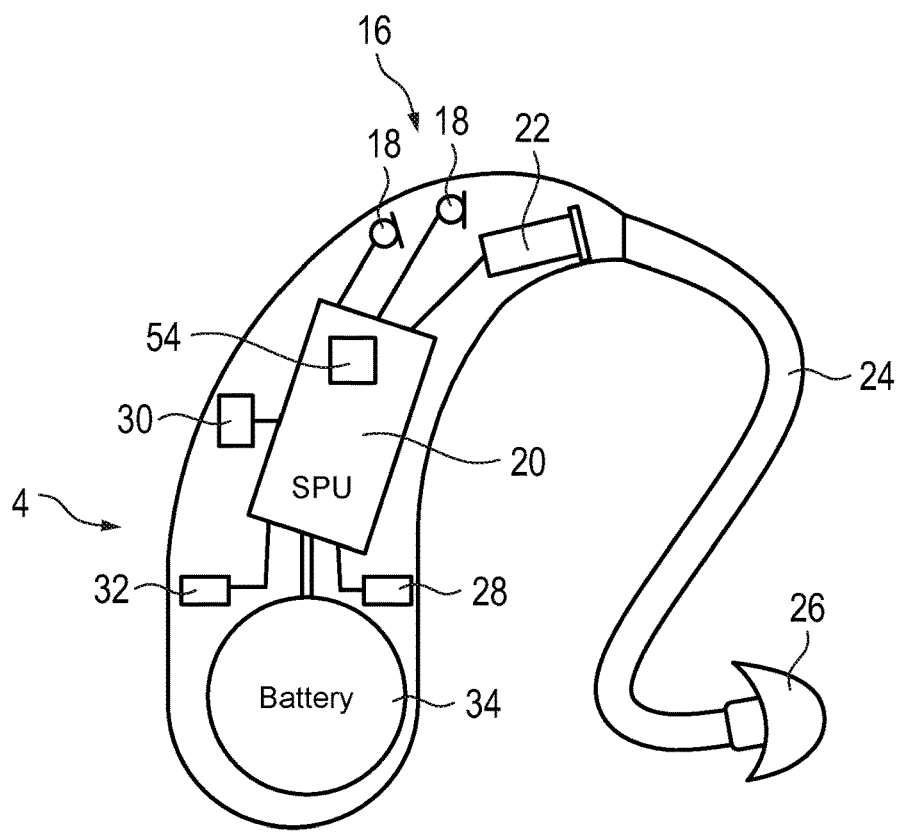
FIG. 2 is an illustration showing the hearing aid.

The hearing aid 4 is schematically shown in FIG. 2. The hearing aid 4 contains a housing 14, which is manufactured from a plastic. A microphone 16 having two microphone units 18 each in the form of electromechanical sound transducers, which are designed as omnidirectional, is arranged inside the housing 14. In that a time offset between the acoustic signals acquired by means of the omnidirectional microphone units 18 is changed, it is made possible to change a directional characteristic of the microphone 16, so that a directional microphone is implemented. The two microphone units 18 are coupled for signaling to a signal processing unit 20, which comprises an amplifier circuit (not shown in greater detail) and a signal processor. The signal processing unit 20 is furthermore formed by means of circuit elements, for example electrical and/or electronic components. The signal processor is a digital signal processor (DSP) and is connected via an A/D converter (not shown in greater detail) for signaling to the microphone units 18.

A receiver 22 is coupled for signaling to the signal processing unit 20. By means of the receiver 22, which is an electromechanical sound transducer, during operation an (electrical) signal provided by means of the signal processing unit 20 is converted into an output sound, thus into soundwaves. These are introduced into a sound tube 24, one end of which is fastened on the housing 14. The other end of the sound tube 24 is enclosed by means of a dome 26, which is arranged in the intended state in an auditory canal (not shown in greater detail here) of the wearer 2 of the hearing aid 4.

Furthermore, a sensor 28 is arranged inside the housing 14, which is an acceleration sensor or at least comprises it. It is thus possible by means of the sensor 28 to measure an acceleration of the housing 14 and also to determine therefrom, in particular by means of integration, a current position of the housing 14. It is also possible here to determine an inclination of the housing 14 and therefore also of a head of the wearer 2. Moreover, a GPS sensor 30 is arranged inside the housing 14, by means of which a current position of the hearing aid 4 and thus also of the wearer 2 can be determined. Moreover, a communication device 32 is arranged inside the housing 14, which meets a Bluetooth standard and by means of which the Bluetooth connection is established with the external device 8.

The signal processing unit 20 is energized by means of a battery 34 arranged in the housing 4. A part of the electrical energy is conducted from the signal processing unit 20 to the sensor 28, the GPS sensor 30, and the communication device 32. The microphone 16 and the receiver 22 are also operated by means of this electrical energy.

Figure 3:
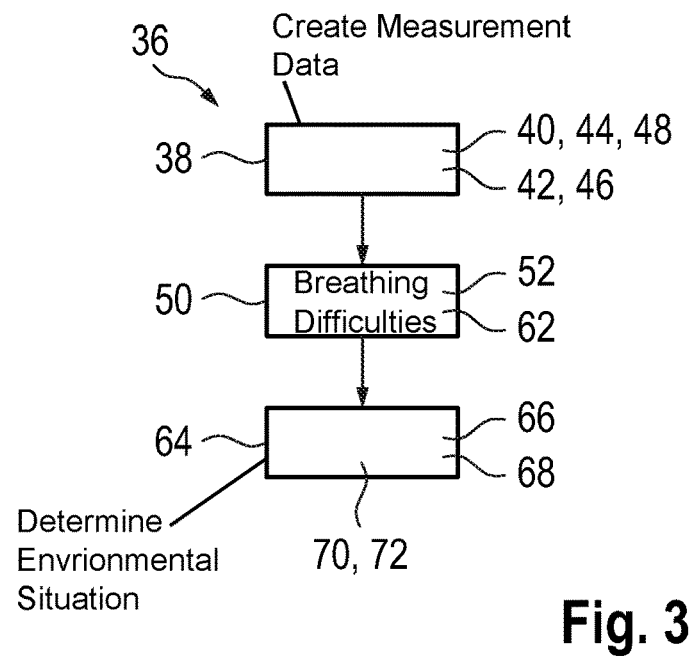
FIG. 3 is a flow diagram showing a method for operating the hearing aid.

The hearing aid 4 is operated according to a method 36 shown in FIG. 3, wherein the method 36 is at least partially carried out by means of the signal processing unit 20, which thus forms a controller or a control unit of the hearing aid 4. In a first work step 38, measurement data 40 are created by means of the sensor 28. In other words, an acceleration and position of the hearing aid 4 are determined and any physical activity of the wearer 2 is inferred therefrom. In other words, it is checked whether the wearer 2 is carrying out or has carried out a physical activity, for which purpose the measurement data 40 are implemented accordingly. A current posture 42 of the wearer band 2 is also determined on the basis of the measurement data 40. In other words, it is determined whether the wearer 2 is currently standing, sitting, or running, and what the attitude of the head of the wearer 2 and possibly also of the torso is.

Furthermore, further measurement data 44 are created by means of the microphone 16. The further measurement data 44 correspond in this case to the sound which reaches the individual microphone units 18 and is registered by means thereof. On the basis of the further measurement data 44, a value 46 characterizing the respiration of the wearer 2 is determined. The characterizing value 46 comprises a respiratory rate of the wearer 2. For this purpose, the breathing noises of the wearer 2, which are present in the further measurement data 44, are analyzed accordingly. The characterizing value 46 also comprises a depth of their inhalation, and the information as to whether their exhalation takes place through lips pressed together. The further measurement data 44 are also analyzed accordingly thereupon.

Moreover, a current position of the hearing aid 4 and thus also of the wearer 2 of the hearing aid 4 is determined in the first work step 38 by means of the GPS sensor. External data 48 are also received via the Bluetooth connection from the external sensor 10, which are transmitted by means of the communication module of the external device 8. The external data 48 relate to the physical condition of the wearer 2 and accordingly their pulse rate.

In a subsequent second work step 50, breathing difficulties 52 of the wearer 2 are inferred on the basis of the measurement data 40 and the further measurement data 44. The severity of the possible breathing difficulties 52 is also determined. A neural network 54 integrated in the signal processing unit 20 is used to infer the breathing difficulties 52. Thus, for example, the breathing difficulties 52 are present when the current posture 42 essentially corresponds to a defined posture 56 or is at least similar thereto, and this is held for a specific time span. In each defined posture 56, the respiration of the wearer 2 is assisted in that certain muscle groups are pre-tensioned due to the posture. A pressure is also sometimes exerted on the abdominal area, so that the required muscles necessary for this purpose are assisted in respiration.

Figure 4:
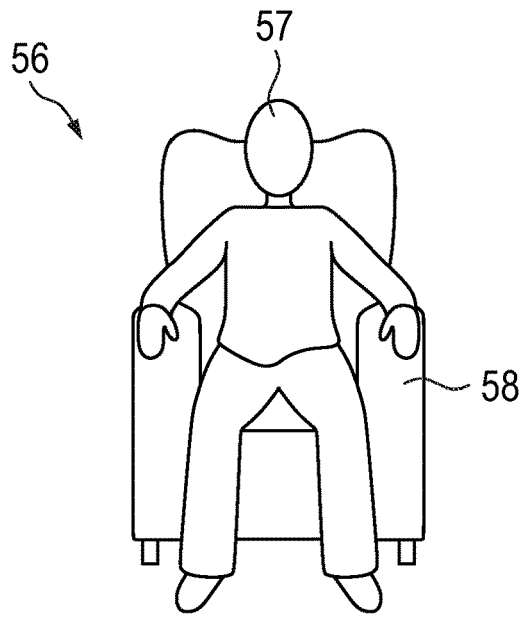
FIGS. 4-9 are illustrations showing different postures assisting the respiration.
Figure 5:
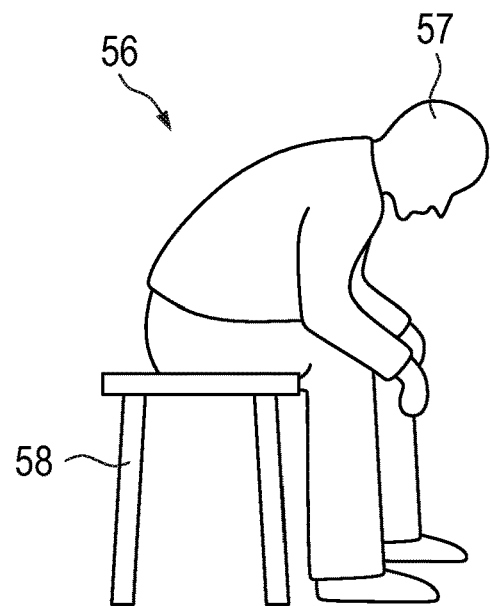
Figure 6:
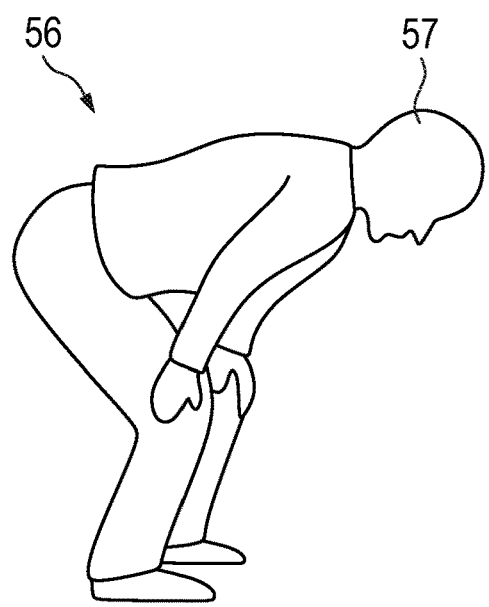
Figure 7:
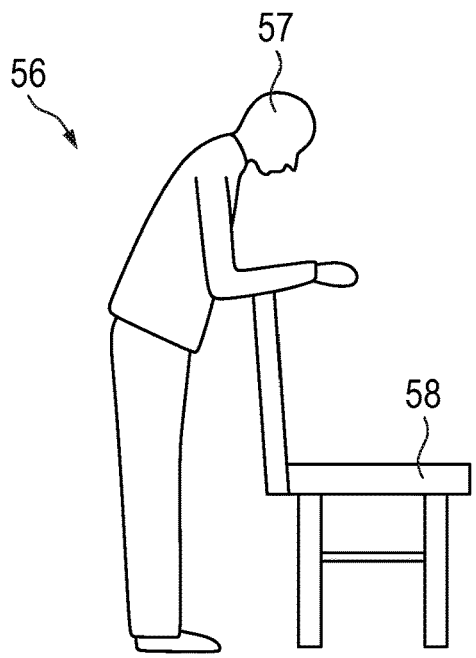
Figure 8:
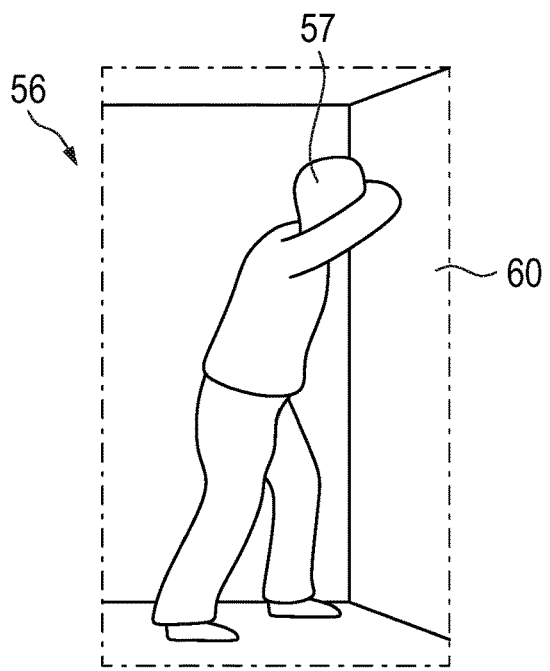
Figure 9:
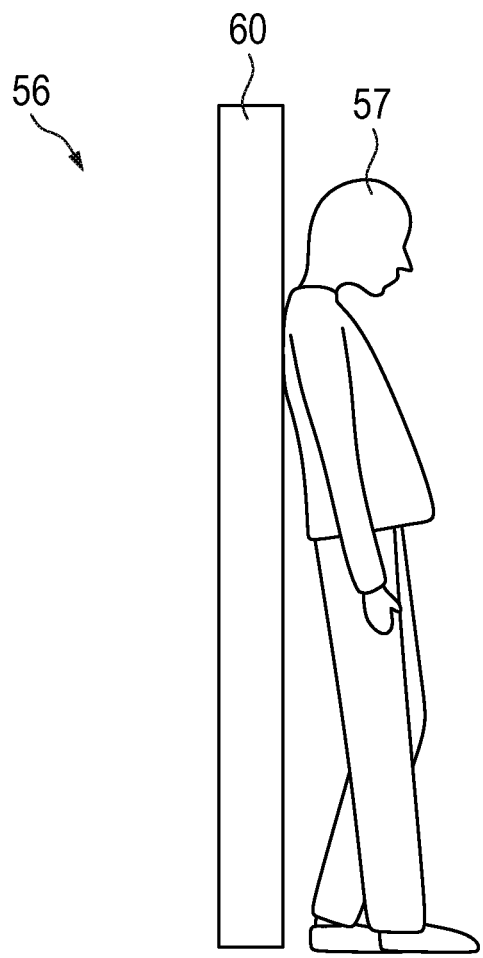

One such defined posture 56 is the so-called pasha position, which is shown in FIG. 4. In this case, the respective person 57 sits with back fully extended on an item of seating furniture 58. The head of the person 57 is inclined slightly downward. Another of the defined postures 56 is schematically shown in FIG. 5 and corresponds to the so-called cart driver position. In this case, the person 57 sits on the seating furniture 58, wherein the torso is inclined forward and the elbows are supported on the thighs. The head of the person 57 is directed downward. In a further such defined posture 56, which is shown in FIG. 6, the person 57 crouches, wherein the legs are spread. The hands are supported on the thighs or the knees. The head of the person 57 is directed downward. In a further variant, which is shown in FIG. 7 and FIG. 8, the torso of the person 57 is inclined forward, wherein the forearms are supported either on a backrest of the seating furniture 58 or a wall 60. The head of the person 57 is inclined downward in each case. In a further variant of the defined posture 56, which is shown in FIG. 9, the torso of the person 57 leans on a wall 60, wherein the head is inclined downward.

If the breathing difficulties 52 are present, one of the defined postures 56 is unconsciously assumed by the wearer 2, so that their respiration is assisted. By means of analysis as to whether the current posture 42 corresponds to one of the defined postures 56, an indication of the presence of the breathing difficulties 52 is given. The neural network 54 is used to check whether the current posture 42 corresponds to one of the defined postures 56.

By means of the neural network 46, in this case the respective current posture 42 is assessed with regard to one of the defined postures 56 in cooperation with the characterizing value 46 and it is derived therefrom whether the breathing difficulties 20 are present. Thus, for example, with equal characterizing value 46 but different current postures 42, the breathing difficulties 52 are inferred differently. Also, for example, if the current posture 42 corresponds to one of the defined postures 56, but the characterizing values 46 differ, the breathing difficulties 52 are inferred differently, thus as to whether they are present or not. In summary, the breathing difficulties 52 are therefore inferred on the basis of the current posture 42 of the wearer 2 and on the basis of the characterizing value 46, for which the neural network 54 is used. Moreover, the severity of the breathing difficulties 52 is determined. The neural network 54 is already trained at the producer but is adapted during the wearing on the wearer 2, for example continuously or in a training phase.

As soon as it has been inferred that the breathing difficulties 52 are present, thus that the wearer 2 suffers from the breathing difficulties 52, such as current shortness of breath, a measure 62 of a risk is determined. The determined severity of the breathing difficulties 52 is used in determining the measure 62. It is also taken into consideration in determining the measure 62 whether the physical activity of the wearer 2 exists or existed. The measure 62 is thus reduced if the wearer 2 carried out a difficult physical activity before the breathing difficulties 52 were inferred. The external data 48, thus the pulse rate, are also used in determining the measure 62. In the case of a comparatively high pulse and existing breathing difficulties 52, wherein no physical activity took place, a high measure 62 is thus used. In contrast, in the case of a reduced pulse and/or if a physical activity of the wearer 2 takes place or took place, a reduced measure 62 is used.

In a subsequent third work step 64, a current environmental situation 66 is determined. For this purpose, the further measurement data 44 are checked for background signals, such as conversing persons. The position determined by means of the GPS sensor 30 is also compared to a map stored in the signal processing unit 20 and therefore the location is determined, at which the wearer 2 is located. It is thus checked, for example, whether the wearer 2 is located at home, in a means of transportation, or, for example, at a cultural event, for example at an opera visit.

Depending on the current environmental situation 66 and depending on the measure 62 for the risk, an activity 68 helping the wearer 2 is carried out, which is also referred to solely as an activity. In the case of a high measure 62, sending an emergency message 70 by means of the communication device 32 is used as a helping activity 68. In the case of such a high measure 62, a life-threatening situation for the wearer 2 is present, so that they need additional help. The emergency message 70, in which the position determined by means of the GPS sensor 30 is also stored, is sent to the external device 8, by means of which the emergency message 70 is passed on by means of the communication module to an emergency call center or rescue services, so that medical emergency personnel can reach the wearer 2. The microphone 16 or the receiver 22 is also activated to output sound, for example, so that persons located in the vicinity of the wearer 2 are made aware of the situation of the wearer 2.

If the measure 62 is less, an output of an instruction 72 is used as the helping activity 68. The receiver 22 is activated accordingly for this purpose, so that the instruction 72 can be perceived by the wearer 2. The instruction 72 relates to assuming a posture 56 assisting the respiration more strongly. If the wearer 2 has already assumed one of the defined postures 56, it is first checked which of the defined postures 56 assists the respiration to a greater extent. This is then communicated by means of the instruction 72 to the wearer 2, for which purpose, for example, either the name of the defined postures 56 or the arrangement of the extremities, such as the arms, is output.

The invention is not restricted to the above-described exemplary embodiment. Rather, other variants of the invention can also be derived therefrom by a person skilled in the art, without leaving the subject matter of the invention. In particular, furthermore all individual features described in conjunction with the exemplary embodiment can also be combined with one another in other ways, without leaving the subject matter of the invention.

The following is a summary list of reference numerals and the corresponding structure used in the above description of the invention.

LIST OF REFERENCE NUMERALS 2 wearer
4 hearing aid
6 ear
8 external device
10 external sensor
12 system
14 housing
16 microphone
18 microphone unit
20 signal processing unit
22 receiver
24 sound tube
26 dome
28 sensor
30 GPS sensor
32 communication device
34 battery
36 method
38 first work step
40 measurement data
42 posture
44 further measurement data
46 characterizing value
48 external data
50 second work step
52 breathing difficulties
54 neural network
56 defined posture
57 person
58 seating furniture
60 wall
62 measure
64 third work step
66 current environmental situation
68 helping activity
70 emergency message
72 instruction

The invention claimed is:

1. A method for operating a hearing aid having a sensor, a microphone, and a receiver, which comprises the steps of:
   inferring breathing difficulties of a wearer on a basis of measurement data created by the sensor and a measure of a risk is determined based on the breathing difficulties;
   determining a current posture of the wearer on a basis of the measurement data and the breathing difficulties being inferred therefrom; and
   carrying out an activity helping the wearer depending on the measure.

2. The method according to claim 1, which further comprises determining a value characterizing a respiration of the wearer on a basis of further measurement data created by means of a microphone and the further measurement data is used to assist in inferring the breathing difficulties.

3. The method according to claim 1, which further comprises using a neural network to infer the breathing difficulties.

4. The method according to claim 1, which further comprises taking into consideration a determined physical activity of the wearer in determining the measure.

5. The method according to claim 1, which further comprises receiving external data relating to a physical state of the wearer from an external sensor and the external data is used in determining the measure.

6. A method for operating a hearing aid having a sensor, a microphone, and a receiver, which comprises the steps of:
- inferring breathing difficulties of a wearer on a basis of measurement data created by the sensor and a measure of a risk is determined based on the breathing difficulties;
- carrying out an activity helping the wearer depending on the measure and includes outputting an instruction for the wearer to assume a posture for more strongly assisting respiration; and
- determining a current environmental situation and the activity helping the wearer is carried out depending on the current environmental situation.

7. The method according to claim 6, wherein the activity helping the wearer further comprises the step of sending an emergency message by means of a communication device.

8. A hearing aid, comprising:
- a sensor;
- a microphone;
- a receiver; and
- the hearing aid is configured to:
  - infer breathing difficulties of a wearer on a basis of measurement data created by said sensor and a measure of a risk is determined based on the breathing difficulties;
  - determine a current posture of the wearer on a basis of the measurement data and the breathing difficulties being inferred therefrom; and
  - carry out an activity helping the wearer depending on the measure.

9. The hearing aid according to claim 8, wherein the hearing aid is a hearing aid device.

* * * * *